(12) United States Patent
Bhaskaran et al.

(10) Patent No.: US 9,149,469 B2
(45) Date of Patent: Oct. 6, 2015

(54) PHARMACEUTICAL COMPOSITION AND A PROCESS THEREOF

(71) Applicant: INDUS Biotech PVT. Ltd., Pune (IN)

(72) Inventors: Sunil Bhaskaran, Pune (IN); Mohan Vishwaraman, Pune (IN)

(73) Assignee: Indus Biotech Pvt. Ltd., Pune (IN)

( * ) Notice: Subject to any disclaimer, the term of this patent is extended or adjusted under 35 U.S.C. 154(b) by 12 days.

(21) Appl. No.: 14/104,976

(22) Filed: Dec. 12, 2013

(65) Prior Publication Data

US 2014/0107167 A1 Apr. 17, 2014

Related U.S. Application Data

(62) Division of application No. 12/041,415, filed on Mar. 3, 2008, now Pat. No. 8,633,229.

(60) Provisional application No. 60/893,075, filed on Mar. 5, 2007.

(51) Int. Cl.
| | |
|---|---|
| *A61K 31/4406* | (2006.01) |
| *A61K 31/198* | (2006.01) |
| *A61K 31/455* | (2006.01) |
| *A61K 36/48* | (2006.01) |
| *A61K 36/74* | (2006.01) |
| *A61K 45/06* | (2006.01) |

(52) U.S. Cl.
CPC ............ *A61K 31/4406* (2013.01); *A61K 31/198* (2013.01); *A61K 31/455* (2013.01); *A61K 36/48* (2013.01); *A61K 36/74* (2013.01); *A61K 45/06* (2013.01)

(58) Field of Classification Search
CPC ............ A61K 31/4406; A61K 31/198; A61K 31/155; A61K 36/48; A61K 36/74; A61K 45/06
See application file for complete search history.

(56) References Cited

U.S. PATENT DOCUMENTS

2005/0226948 A1* 10/2005 Lee et al. ................... 424/757

FOREIGN PATENT DOCUMENTS

WO WO2004/100968 * 11/2004 ............. A61K 35/78

OTHER PUBLICATIONS

Ahmed M.A. Abd-el Mawla, et al, Elicitation of Trigonelline and 4-hydroxyisoleucine with Hypoglycemic Activity in Cell Suspension Cultures of Trigonella foenum graceum L., 2 The Open Conference Proceedings Journal 80, 81 (2011).*

* cited by examiner

*Primary Examiner* — Sean Basquill
(74) *Attorney, Agent, or Firm* — Fenwick & West LLP (57) ABSTRACT

The present invention relates to a pharmaceutical composition having dopaminergic activity and other related pharmaceutical activities comprising trigonelline or its derivative(s) and 4-hydroxyisoleucine or its derivative(s), optionally along with excipients(s); a process of preparing a pharmaceutical composition comprising trigonelline or its derivative(s) and 4-hydroxyisoleucine or its derivative(s), optionally along with excipients(s), wherein the process comprising steps of: (a) extracting a clear solution containing trigonelline and 4-hydroxyisoleucine from plant source; and (b) optionally precipitating derivative(s) of trigonelline and 4-hydroxyisoleucine from the clear solution and obtaining said composition; and an in-vitro method to increase levels of dopamine or to inhibit prolactin by allowing composition comprising trigonelline or its derivative(s) and 4-hydroxyisoleucine or its derivative(s) to bind to cell receptors.

15 Claims, 3 Drawing Sheets

PHARMACEUTICAL COMPOSITION AND A PROCESS THEREOF

CROSS-REFERENCE TO RELATED APPLICATION

This application claims priority to U.S. patent application Ser. No. 12/041,415 filed on Mar. 3, 2008, which claims the benefit of U.S. Provisional Patent Application No. 60/893,075 filed on Mar. 5, 2007, all of which are herein incorporated by reference in their entirety.

FIELD OF THE INVENTION

This invention relates to a novel composition and a preparation thereof from natural sources. This invention also relates to the application of a novel composition as a Dopaminergic agent with applications in the management of dopamine related disorders including Parkinson's disease.

This invention also relates to applications associated with a decrease of prolactin as a prolactin-inhibiting compound, a muscle relaxant, to decrease side-effects caused by anti-psychotic drugs, to decrease sexual dysfunction caused by increased Prolactin and as a compound, which enhances mental alertness.

BACKGROUND AND PRIOR ART OF THE INVENTION

Dopamine is a hormone and a neurotransmitter present in both vertebrates and invertebrates. Chemically it is a phenethylamine present in the brain and acts as a neurotransmitter which activates specific dopamine receptors (D1-D5). Dopamine has many functions in the brain, including important roles in behavior and cognition, motor activity, motivation and reward, regulation of milk production, sleep, mood, attention, and learning. Dopamine plays a major role in appetite, Sociability, Salience, Behavior disorders, Latent inhibition and creative drive. Dopamine is also involved in regulating prolactin secretion.

Inadequate levels of dopamine trigger symptoms like tremors, rigidity and bradykinesia (slowness of movement). In healthy subjects, neurons produce and release dopamine in the brain and other parts of the body. When the dopamine is released by one neuron, it is received by the receptors of the next neuron. This chain reaction eventually leads to the stimulation of nerves. Various neurological disorders can interfere with dopamine production and cause the dopamine levels in the brain to drop. Abnormal levels of dopamine also cause a number of disorders, some of which are chronically degenerative (like Parkinson's disease).

Dopamine strongly influences both motor and thinking areas of the brain. One type of Dopamine works in the movement and motor system. When levels of dopamine decrease below the "normal range" motor and gross-movement problems set in. Very low levels of Dopamine in the motor areas of the brain are known to produce Parkinson's Disease with symptoms such as: muscle rigidity and stiffness, stooped/unstable posture, loss of balance and coordination, gait (walking pattern) disturbance, slow movements and difficulty with voluntary movements, Small-step gait/walking, aches in muscles, tremors and shaking, fixed, mask-like facial, expression, slow, monotone speech, impairment of fine-motor skills, falling when walking and an impairment in cognitive/intellectual ability Low levels of dopamine impair the ability to focus on an environment or to "lock on" to tasks, activities, or conversations. Low levels of Dopamine make concentration and focus very difficult and are also associated with Attention-Deficit Hyperactivity Disorder (ADHD).

Dopamine also plays a major role in inhibiting prolactin secretion. Prolactin is a peptide hormone secreted by the lactotroph cells in the pituitary gland. Prolactin plays a major role in inducing lactation and sexual gratification (which is caused by low levels for dopamine. Adequate levels of dopamine are required for sexual arousal). Dopamine serves as the major prolactin-inhibiting factor and is secreted into portal blood by hypothalamic neurons, binds to receptors on lactotrophs, and inhibits both the synthesis and secretion of prolactin. Increased levels of prolactin have many ill effects like infertility, polycystic ovary syndrome (PCOS), headaches, reduced sex drive and vision problems. High prolactin levels are caused due to many factors including physical and mental stress. Hence a dopaminergic compound (one that increases dopamine levels) will play a key role in regulating (limiting) the levels of prolactin thereby managing the various effects of high levels of prolactin.

It is found that chronic and strenuous exercise as practiced by athletes, body builders and sportsman also leads to an increase in prolactin level. This increased prolactin decreases their sexual libido and induces sexual dysfunction. Therefore dopaminergic agents can be used for decreasing the levels of prolactin and thereby eliminating the side effects by maintaining this hormone within physiological limits.

Dopaminergic agents can be used as a muscle relaxant as it inhibits the excitation caused by acetylcholine. Therefore the Dopaminergic substance of this invention can be used as a muscle relaxant in exercise physiology, anesthesia and in case of muscle spasms.

One of the major effects of low levels of dopamine is Movement Disorders. Movement disorders are a group of diseases and syndromes affecting the ability to produce and control movement. To produce any form of movement even simple motions requires the coordination and action of a complex network of signals. Disruption of any portion of this system can cause a person to produce movements that are too weak, too forceful, too uncoordinated, or too poorly controlled for the task at hand. Unwanted movements may occur at rest or intentional movements may become impossible. Such conditions are called movement disorders.

In some cases, the abnormal movements are the only symptoms of low levels of dopamine. Disorders causing abnormal movements include: Parkinson's disease, Parkinsonism caused by drugs or poisons, Parkinson-plus syndromes (progressive supranuclear palsy, multiple system atrophy, and cortical-basal ganglionic degeneration).

These disorders are caused due to a lack or excess of the neurotransmitter Dopamine. Drug therapy can help compensate for some imbalances of the basal ganglionic circuit. Acetylcholine is an excitatory chemical that helps regulate dopamine in the brain. In the body, acetylcholine released at nerve endings causes muscle contraction.

Parkinson's is a progressive degenerative disease, which destroys dopamine-producing cells and leads to a problem in coordinated movement. It is characterized by tremor, rigidity, Akinesia and postural instability. The main biochemical abnormality is the depletion in Dopamine and which causes an imbalance between acetylcholine and dopamine. Causes of Parkinson's are not known clearly. There is weak hereditary link in few cases. It is also caused by an environmental toxin MPTP (Methyl phenyl tetra-hydro pyridine), which is used as a pesticide.

Parkinson's disease is usually a disorder of the elderly occurring after the age of 65. It is caused by the death of a group of nerve cells in the brain called the "Substantia Nigra" or black substance because they look dark in appearance. The nerve process from these cells normally extends up to another area of brain called the striatum, where they make connections and release a chemical called Dopamine as their Neurotransmitter.

The Substantia Nigra and the striatum help to control movement, including our ability to initiate movement. With the loss of the Nigrostriatal pathway, the Parkinson's patient has extreme difficulty in performing such acts like getting out of a chair and starting to walk. They also experience increased tremor and rigid muscles.

Current methods of treatment for dopamine related diseases (eg: Parkinson's and diseases related to low levels of dopamine) include:

L-Dopa (Dihydroxy Phenyl Alanine)

Since the cause of Parkinson's disease is a loss of Dopamine releasing nerve cells, one approach to treating this disorder is to restore the levels of Dopamine in the brain. Dopamine will not pass from the blood into the brain. Within nerve cells, dopamine is produced by a series of chemical reactions catalyzed by enzymes. The last stage in the sequence is the formation of dopamine from the amino acid L-Dopa. L-Dopa easily crosses into the brain from blood. The most popular and effective treatment for Parkinson's is the administration of L-Dopa in tablet form.

L-Dopa gets into blood stream and passes into brain. In the brain Dopa decarboxylase converts this into Dopamine. L-Dopa produces a very marked improvement in general movement, facial expression and body posture. However, it has very poor effect on tremor, swallowing, balance and the slow initiation of movements.

Combining Other Drugs with L-Dopa

The enzyme Dopa Decarboxylase that converts L-Dopa to Dopamine exists in blood and body tissues. Therefore, L-Dopa degrades in the serum to the extent of 90%. This is blocked by inhibiting this enzyme by other drugs like Carbidopa and Benseraside. These are combined with L-Dopa to increase its brain availability. Carbidopa and Benseraside do not pass into the brain.

Tolcapone and Entacalpone

L-Dopa is also destroyed by another enzyme COMT (Catechol O-Methyl Transferase). These drugs inhibit COMPT and make L-Dopa available to brain. But these drugs have long term problem with L-Dopa. On long term administration of L-Dopa, patients may experience fluctuations in its effect. There may be greater delay in the onset of action and drug action period may get shortened. Patients also experience on off periods. This implies that the patients may function perfectly well for long hours after the drug administration and they might find that the effect of the drug stops abruptly.

Side effects of L-Dopa: Most patients feel nausea; prolonged use of this can induce Schizophrenia, especially hallucinations and disturbed sleep. Continued use also leads to slow and involuntary movements.

MAO Inhibitions (Monoamine Oxidase)

An alternative to increasing the formation of dopamine in the brain is by administering L-Dopa to decrease the breakdown of dopamine. Dopamine is broken down by an enzyme Monoamine Oxidase (MAO), particularly MAO-B. Deprenyl is a MAO-B inhibiting.

Receptor Agonists

It is possible to compensate for the loss of Dopamine by using drugs which act directly on Dopamine receptors. Drugs like Bromocriptine, Lisuride are Receptor Agonists. They stimulate the receptors which respond to dopamine and act as replacements for the Dopamine normally released by the Nigrostriatal neurons. These drugs induce a range of involuntarily movements and act on dopamine receptors in the pituitary gland, a part of the brain, which controls many important hormone secretions. The side effects of the activation of Dopamine receptors to suppresses the release of the hormone prolactin are infertility and menstrual disorders.

Anticholinergic Drugs

Within the striatum of the brain, both dopamine and Acetylcholine are neurotransmitters. Dopamine causes inhibition of nerve cells while acetylcholine causes their excitation. When the brain loses Dopamine cells, the activity of acetylcholine is intact. Therefore one strategy is to reduce acetylcholine and balance its effect along with the effect of Dopamine. Anticholinergic drugs are more effective in reducing tremors, although they have no effect on muscular rigidity and difficulty of movement. These drugs have many side effects like dry mouth, blurred vision, constipation, difficulty in urination etc.

U.S. Pat. No. 4,880,816 describes a compound where dopamine is chemically combined to another molecule DHC, particularly of a trigonelline which has blood brain barrier penetration property. Here, DHC compounds acts as an adjunct to dopamine to cross the blood brain barrier and gets broken and eliminated. Thus, it does not define any dopaminergic action for trigonelline.

Current therapy targets symptomatic relief and no agent is capable of inhibiting neuronal degeneration. There is urgent need for a kinder and gentler therapy for long-term management with minimal side effect and with optimum efficiency. The present invention addresses this urgent need for a Dopaminergic product, which can be effectively utilized for the management of diseases associated with the lack of dopamine including Parkinson's disease.

A major disadvantage of anti-psychotic drugs is their blocking the D2 receptor of dopamine. Thus these drugs lead to the side effect of movement disorders linked to blockage of dopamine receptor D2 in the brain. Hence a dopaminergic agent would be the answer to the immobility caused as a side effect of anti-psychotic drugs.

OBJECTS OF THE INVENTION

The main object of the present invention is to obtain a pharmaceutical composition having dopaminergic activity and other related pharmaceutical activities.

Another main object of the present invention is to obtain a pharmaceutical composition comprising trigonelline or its derivative(s) and 4-hydroxyisoleucine or its derivative(s) optionally along with excipients(s).

Yet another object of the present invention is to develop a process of preparing a pharmaceutical composition comprising trigonelline or its derivative(s) and 4-hydroxyisoleucine or its derivative(s), optionally along with excipients(s).

Still another object of the present invention is to extract trigonelline and 4-hydroxyisoleucine from plant source.

Still another object of the present invention is to obtain a method of treating dopamine related diseases by administering a therapeutically effective amount of a pharmaceutical composition comprising trigonelline or its derivative(s) and 4-hydroxyisoleucine or its derivative(s), optionally along with excipients(s) in a subject in need thereof.

Still another object of the present invention is to obtain a method of treating ill effects caused by prolactin by administering a therapeutically effective amount of a pharmaceutical composition comprising trigonelline or its derivative(s) and 4-hydroxyisoleucine or its derivative(s), optionally along with excipients(s) in a subject in need thereof.

Still another object of the present invention is to obtain a method of treating side-effects caused by dopamine receptor antagonists by administering a therapeutically effective amount of a pharmaceutical composition comprising trigonelline or its derivative(s) and 4-hydroxyisoleucine or its derivative(s), optionally along with excipients(s) in a subject in need thereof.

STATEMENT OF THE INVENTION

Accordingly, the present invention relates to a pharmaceutical composition having dopaminergic activity and other related pharmaceutical activities comprising trigonelline or its derivative(s) and 4-hydroxyisoleucine or its derivative(s), optionally along with excipients(s); a process of preparing a pharmaceutical composition comprising trigonelline or its derivative(s) and 4-hydroxyisoleucine or its derivative(s), optionally along with excipients(s), wherein the process comprising steps of: (a) extracting a clear solution containing trigonelline and 4-hydroxyisoleucine from plant source; and (b) optionally precipitating derivative(s) of trigonelline and 4-hydroxyisoleucine from the clear solution and obtaining said composition; a method of treating dopamine related diseases, said method comprising administering a therapeutically effective amount of a pharmaceutical composition comprising trigonelline or its derivative(s) and 4-hydroxyisoleucine or its derivative(s), optionally along with excipients(s) in a subject in need thereof; a method of treating ill effects caused by prolactin, said method involves prolactin inhibition by administering a therapeutically effective amount of a pharmaceutical composition comprising trigonelline or its derivative(s) and 4-hydroxyisoleucine or its derivative(s), optionally along with excipients(s) in a subject in need thereof; and a method of treating side-effects caused by dopamine receptor antagonists, said method comprising administering a therapeutically effective amount of a pharmaceutical composition comprising trigonelline or its derivative(s) and 4-hydroxyisoleucine or its derivative(s), optionally along with excipients(s) in a subject in need thereof.

DETAILED DESCRIPTION OF THE INVENTION

The present invention relates to a pharmaceutical composition having dopaminergic activity and other related pharmaceutical activities comprising trigonelline or its derivative(s) and 4-hydroxyisoleucine or its derivative(s), optionally along with excipients(s).

In another embodiment of the present invention, the concentration of trigonelline or its derivative(s) ranges between 30% to 90% and the concentration of 4-hydroxyisoleucine or its derivative(s) ranges between 10% to 30%.

In yet another embodiment of the present invention, the trigonelline is obtained from plant or animal source.

In still another embodiment of the present invention, the trigonelline is obtained from *Trigonella foenum graecum* and *Coffee arabica*.

In still another embodiment of the present invention, the derivative(s) of trigonelline are selected from a group comprising hydrochloride derivatives, acetate derivatives, citrate derivatives, benzoate derivatives, salt derivatives and acid derivatives, preferably hydrochloride derivatives.

In still another embodiment of the present invention, the 4-hydroxyisoleucine is obtained from plant source, preferably *Trigonella foenum graecum*.

In still another embodiment of the present invention, the derivative(s) of 4-hydroxyisoleucine are selected from a group comprising hydrochloride derivatives, acetate derivatives, citrate derivatives, benzoate derivatives, salt derivatives and acid derivatives, preferably hydrochloride derivatives.

In still another embodiment of the present invention, the excipients(s) are selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents and speheronization agents.

In still another embodiment of the present invention, the composition is formulated into dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, phytoceuticals, nutraceuticals and food stuffs.

In still another embodiment of the present invention, the other related pharmaceutical activities are selected from a group comprising inhibition of prolactin, muscle relaxation, role as precursor of catecholamines and decrease in sexual dysfunction and the side-effects caused by anti-psychotic drugs.

The present invention also relates to a process of preparing a pharmaceutical composition comprising trigonelline or its derivative(s) and 4-hydroxyisoleucine or its derivative(s), optionally along with excipients(s), wherein the process comprising steps of:
1) extracting a clear solution containing trigonelline and 4-hydroxyisoleucine from plant source; and
2) optionally precipitating derivative(s) of trigonelline and 4-hydroxyisoleucine from the clear solution and obtaining said composition.

In still another embodiment of the present invention, the concentration of trigonelline or its derivative(s) ranges between 30% to 90% and the concentration of 4-hydroxyisoleucine or its derivative(s) ranges between 10% to 30%.

In still another embodiment of the present invention, the excipient(s) are selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents and speheronization agents.

In still another embodiment of the present invention, the derivative(s) are selected from a group comprising hydrochloride derivatives, acetate derivatives, citrate derivatives, benzoate derivatives, salt derivatives and acid derivatives, preferably hydrochloride derivatives.

In still another embodiment of the present invention, the clear solution is extracted from the plant *Trigonella foenum graecum* and/or *Coffea arabica* comprising steps of:
 a. flaking seeds of *Trigonella* and/or *Coffea arabica*;
 b. defatting flaked *Trigonella* seeds using hexane solvent;
 c. passing a solvent mixture of aliphatic alcohol and water through the flaked seeds to extract a solvent containing trigonelline and amino acid(s);
 d. vacuum concentrating the solvent to obtain semisolid mass;
 e. dissolving the semisolid mass in deionized water to obtain a clear solution;
 f. passing the clear solution of step (e) through an ion exchange resin column to retain the amino acids and the trigonelline;
 g. eluting the column and concentrating the eluent to obtain resultant mass;
 h. drying the clear solution of the resultant mass to obtain a free flowing powder; and
 i. dissolving the powder in a solvent to obtain said clear solution containing trigonelline and amino acid(s).

In still another embodiment of the present invention, the seeds are flaked to a size preferably of about 2 mm thickness.

In still another embodiment of the present invention, the solvent mixture comprises an aliphatic alcohol and water in ratio of 1:9 to 9:1, preferably 7:3.

In still another embodiment of the present invention, the aliphatic alcohol is ethanol.

In still another embodiment of the present invention, the column is eluted with aqueous or alcoholic solution of ammonia.

In still another embodiment of the present invention, the solvent is selected from a group comprising heterocyclic aromatic compounds, aliphatic compounds, ketones, cyanides, alcohols, nitriles, esters, ether and mixtures of one or more thereof.

In still another embodiment of the present invention, the solvent is ethanol.

In still another embodiment of the present invention, the concentration is carried at a temperature ranging from 40° C. to 80° C.

In still another embodiment of the present invention, the amino acid is 4-hydroxyisoleucine.

The present invention also relates to a method of treating dopamine related diseases, said method comprising administering a therapeutically effective amount of a pharmaceutical composition comprising trigonelline or its derivative(s) and 4-hydroxyisoleucine or its derivative(s), optionally along with excipients(s) in a subject in need thereof.

In still another embodiment of the present invention, the subject is animal including human beings.

The present invention also relates to a method of treating ill effects caused by prolactin, said method involves prolactin inhibition by administering a therapeutically effective amount of a pharmaceutical composition comprising trigonelline or its derivative(s) and 4-hydroxyisoleucine or its derivative(s), optionally along with excipients(s) in a subject in need thereof.

In still another embodiment of the present invention, the ill effects caused by prolactin are selected from a group comprising infertility, polycystic ovary disease and increased lactation.

In still another embodiment of the present invention, the subject is animal including human beings.

The present invention also relates to a method of treating side-effects caused by dopamine receptor antagonists, said method comprising administering a therapeutically effective amount of a pharmaceutical composition comprising trigonelline or its derivative(s) and 4-hydroxyisoleucine or its derivative(s), optionally along with excipients(s) in a subject in need thereof.

In still another embodiment of the present invention, the side-effects are the movement disorders caused by blockage of dopamine receptor by dopamine receptor antagonists.

In still another embodiment of the present invention, the subject is animal including human beings.

One embodiment of the present invention relates to the use of a composition for the manufacture of a medicament with dopaminergic activities, comprising trigonelline, it derivatives, 4 hydroxyisoleucine, its derivatives and optionally with excipients(s). The trigonelline can be derived from botanical and animal sources. This composition is used for increasing dopamine concentration in the brain and therefore improving the conditions associated with low dopamine levels such as parkinsons disease, movement disorders etc. This composition is used for activities related to prolactin inhibition, stopping lactation, muscle relaxation, decreases sexual dysfunction, increasing mental alertness and other dopamine related functions. Another aspect of this embodiment is that the composition having dopaminergic activity is a selective Monoamine oxidase B inhibitor. Another aspect of the present invention is that the composition having dopaminergic activity has no interaction with Tyramine containing substances and thus does not increase blood pressure when the subject ingests materials with high levels of tyramine.

Another embodiment of the present invention relates to the use of a composition for the manufacture of a medicament with dopaminergic activity which is capable of inhibiting prolactin levels in a subject in need thereof. Still another aspect of the present embodiment is related to the use of the composition for the treatment of polycystic ovary disease. Still another aspect of the present embodiment relates to the use of the composition for the manufacture of a medicament for the treatment of infertility. Still another aspect of the present embodiment is to manufacture a medicament for the regulation of the levels of human sex hormones.

Another embodiment of the present invention relates to the use of the composition having dopaminergic activity for the manufacture of a medicament to minimize the harm caused by dopamine receptor antagonists thereby inducing immobility.

Another embodiment of the invention relates to a composition having dopaminergic and pharmaceutical activity comprising trigonelline, derivatives of trigonelline, 4 hydoxyisoleucine, its derivatives and excipients.

The composition of the present invention comprising trigonelline or its derivative(s) and 4-hydroxyisoleucine or its derivative(s) optionally along with excipients(s) is herein also referred as test drug or test compound or test drug composition in the specification.

The major advantage of the present embodiments of the present invention is that the test drug is a Monoamine Oxidase-B inhibitor. Due to this selectivity it does not elicit a response with dietary tyramine thus preventing the "cheese reaction" which is a major side effect of non-selective MAO inhibitors. A second advantage is the fact that this composition having dopaminergic activity can reduce the side effects of antipsychotic drugs. Thirdly, this composition can also inhibit prolactin secretion which is a major advantage.

The present invention describes in detail the procedure for isolating and purifying a chemical marker from such botanical as *Trigonella foenum greacum* and *Coffea arabica* (botanical name). The chemical marker is the alkaloid Trigonelline and is extracted as its Hydrochloride, Acetate, Citrate, sulfonate, mesylate, hydroiodide Benzoate or a salt of an acid both mineral and organic, but preferably as Hydrochloride. This purified extract is studied for its bioactivity in various classical animal models. A novel aspect of this compound is that it has a Dopamine like activity as confirmed by several specific animal experiments as per approved protocols. Thus, it has been proved for the first time that the compound trigonelline shows dopaminergic activity through our invention.

The brief summary of one embodiment is:
  a. Trigonelline containing seeds for example fenugreek seeds or *Coffea arabica* seeds are flaked to expose the inner core so as to ensure effective defatting, extraction and processing.
  b. Hexane solvent is passed through the fenugreek bed repeatedly to achieve effective defatting of the fenugreek. This operation need not be carried out for *Coffea Arabica* seeds.
  c. The flaked seeds are loaded in a percolater and solvent mixture comprising of an aliphatic alcohol and water are passed through the layer to achieve effective extraction of the Trigonelline and amino acids (4 hydroxyisoleucine) along with Saponin.
  d. The solvent is vacuum concentrated at lower temperatures to ensure the integrity of the mass and the resultant mass is dissolved in deionised water to get clear solution.
  e. The clear solution thus obtained is passed through a strong acid cation exchange resin in Gel form to retain the amino acids and Trigonelline.
  f. The column is washed free of all impurities and colors using deionised water and the column is eluted with an aqueous solution or alcoholic solution of ammonia with strength of 5N concentration.
  g. The eluted compound in the solvent elute is concentrated under vacuum to remove the water and solvent and the resultant mass is dissolved and filtered to get a clear solution.
  h. The clear solution obtained is spray dried to get a free flowing powder and maybe used as such.
  i. The powder is re-dissolved in either isopropyl alcohol or ethyl alcohol to get clear solution.
  j. The purified extract is subjected to HPLC measurement to confirm the assay.

Further, the clear alcoholic solution can optionally be subjected to a gas stream of Hydrogen chloride to convert trigonelline and 4-hydroxyisoleucine into their respective hydrochloride derivatives.

A purified extract of the above compound as Trigonelline and/or its derivative and 4 hydroxyisoleucine and/or its derivatives is administered to Swiss Albino mice as per a Haloperidol Protocol. This induces Parkinson's symptoms. This extract reversed these symptoms in a dose dependent manner confirming Dopaminergic or dopamine like activity of this extract.

A purified extract of the above compound as Trigonelline and/or its derivative and 4 hydroxyisoleucine and/or its derivatives is administered to Swiss Albino mice to examine the affect of this in Oxotremorine Antagonism Mechanism. This confirms a mild Anticholinergic activity, which makes this eminently suitable for Parkinson's treatment.

The Dopamine effect combined with mild Anticholinergic effect is the best methodology for treatment of dopamine related disorders including Parkinson's disease. Parkinson's is not only brought about by depletion of Dopamine, but is also caused by the imbalance of Dopamine and Acetylcholine Dopamine is a precursor for Epinephrine and Norepinephrine. Therefore, this compound can increase the concentration of Epinephrine and increase mental alertness and performance. Dopamine is an inhibitory neurotransmitter. This can control the effects of Acetylcholine. The proposed extract and compound can be used for the purpose of muscle relaxation in exercise physiology.

Dopaminergic substances reduce the hormone prolactin levels. Prolactin is implicated in sexual dysfunction. This compound can be used for inhibiting prolactin. Prolactin induces lactation in nursing mothers. Dopaminergic substances inhibit Prolactin. This compound can be used for stopping lactation.

In another embodiment of the present invention, the composition having dopaminergic activity is derived from botanical sources.

1. Fenugreek seeds or any other seeds containing Trigonelline like *Coffea arabica* seeds were flaked using roller flaking machine to a size of thickness varying between 1 mm to 4 mm size. The effective exposure of the inner core was achieved by flaking to a size preferably of 2 mm thickness. The flaked seeds were packed in an extractor fitted with bottom filter of suitable mesh size preferably 100 mesh to ensure that the seed meal is not allowed to move along with the solvent. Hexane is allowed to percolate through the packed seed layer.

2. The percolated solvent is recycled efficiently over period of 8 to 10 hrs so that the resultant fenugreek meal is free of oils & lipids. This delipidification procedure need not be carried out on *Coffea arabica* seeds.

3. The Hexane extracted meal is re-extracted with a solvent mixture comprising an aqueous aliphatic alcohol in a ratio of 1:9 to 9:1. Preferably 7:3 as the solvent. In the case of *Coffea arabica* seeds the alcohol solvent can be reduced to have a minimum composition of alcohol say nine parts of water to one part of alcohol. The said alcohol may be methyl alcohol, Ethyl alcohol, Isopropanol and preferably ethanol as the alcoholic solvent. The aqueous alcohol mixture is passed from top to bottom through the fenugreek layer in the percolater. The process of recycling the solvent was continued for a period of time ranging between 8 hrs to 10 hrs preferably 8 hrs at room temperature. The clear extract from the bottom of the percolater is inspected visually for any suspended particles and refiltered if necessary.

4. The clear filtrate is vacuum concentrated at a temperature ranging between 50° C. to 75° C. preferably at 55° C., to a pasty mass and the solvent recovered. The paste is redissolved in deionised water to get a clear solution consisting of around 5% solid content.

5. The clear solution is passed through an Ion Exchange resin column consisting of a strong acid anion in gel form and eluted with 5N aqueous ammonia solution. The column can also be eluted with aqueous alcoholic ammonia solution preferably Ethanol, Isopropanol, or methanol in the ratio of 1:1.

6. The desorbed solution is vacuum concentrated to 50% solid content and spray dried in a co-current spray dryer to powder. Optionally the powder obtained by the above manner is dissolved in ethyl alcohol or isopropyl alcohol in the ratio of 1:20 of powder to alcohol ratio and is then filtered.

7. Optionally, the clear filtrate is cooled to low temperature between 0° C. to 5° C. preferably at 0° C. and a dry stream of Hydrogen chloride gas is passed through it to precipitate Trigonelline and 4 hydroxyisoleucine as their respective hydrochloride derivatives. The precipitated derivatives are filtered and washed clean of impurities and dried under vacuum between 60° C. to 90° C.

The invention is further elaborated with the help of following examples. However, these examples should not be construed to limit the scope of the invention.

Example 1

1000 grams of fenugreek seeds having a moisture content less than 5% were flaked in a roller flaker to a thickness of 2 mm The flaked material is stalked in a column having a bed height of 300 mm. 5 liters of hexane was passed through the layer of fenugreek and the eluent collected from the bottom is recycled through the fenugreek layer for a period of 10 hrs at 35° C. After 10 hrs the fenugreek layer was drained free of hexane. Solvent mixture (8 liters) comprising of Isopropyl alcohol and water in the ratio of 4:1 was passed through the layer for a period of 8 hrs at 35° C. by recycling the eluent. After 8 hrs the fenugreek bed is drained free of extracts and all the collected extracts were concentrated to semisolid mass under vacuum at 50° C.

The concentrated mass is redissolved in 5 liters of deionised water to get a clear solution. The clear aqueous solution was passed through a column containing 400 ml of strong acid cation exchange Gel type resin for 2 hrs. TLC screening for the absence of Trigonelline checked on the column eluent using a system consisting of n-Butanol:Acetic acid:Water in the ratio of 12:8:4 as the mobile phase on silica Gel precoated plate F254 (1.05554.007) and observation under UV 254 nm. After saturation of the column the resin bed was washed free of colors and adhering impurities using 4 liters of deionised water. The column is desorbed using 800 ml of aqueous ammonia of 5N strength, at a rate of 400 ml per hour. The mixture eluted out is concentrated under vacuum at 45° C. to a semisolid mass.

The dried mass is redissolved in 150 ml of deionised water and filtered free of insoluble. The solution is concentrated under vacuum at 50° C. to a solid content of 20% and spray dried in a co-current indirect hot air spray dryer under following conditions.
Inlet temperature: 160° C.
Outlet temperature: 80° C.
Atomizer RPM: 12000
The yield is 9 gms. (The HPLC showed 25% Trigonelline & 35% amino acids)

The above material is redissolved in 250 ml of Ethyl alcohol, filtered through 41Whatmann filter paper and cooled to 0° C. At that temperature a dry stream of Hydrogen chloride gas is passed through this to precipitate the Trigonelline hydrochloride. The precipitate was filtered out on filter paper and washed with cold ethyl alcohol and dried under vacuum at 60° C.

Example 2

1000 grams of fenugreek seeds having a moisture content less than 5% were flaked in a roller flaker to a thickness of 2 mm The flaked material is stalked in a column having a bed height of 300 mm. 5 liters of hexane was passed through the layer of fenugreek and the eluent collected from the bottom is recycled through the fenugreek layer for a period of 10 hrs at 35° C. After 10 hrs the fenugreek layer was drained free of hexane. Solvent mixture (8 liters) comprising of Isopropyl alcohol and water in the ratio of 4:1 was passed through the layer for a period of 8 hrs at 35° C. by recycling the eluent. After 8 hrs the fenugreek bed is drained free of extracts and all the collected extracts were concentrated to semisolid mass under vacuum at 50° C.

The concentrated mass is redissolved in 5 liters of deionised water to get a clear solution. The clear aqueous solution was passed through a column containing 400 ml of strong acid cation exchange Gel type resin for 2 hrs. TLC screening for the absence of Trigonelline checked on the column eluent using a system consisting of n-Butanol:Acetic acid:Water in the ratio of 12:8:4 as the mobile phase on silica Gel precoated plate F254 (1.05554.007) and observation under UV 254 nm. After saturation of the column the resin bed was washed free of colors and adhering impurities using 4 liters of deionised water. The column is desorbed using 800 ml of aqueous ammonia of 5N strength, at a rate of 400 ml per hour. The mixture eluted out is concentrated under vacuum at 45° C. to a semisolid mass.

The dried mass is redissolved in 150 ml of deionised water and filtered free of insoluble. The solution is concentrated under vacuum at 50° C. to a solid content of 20% and spray dried in a co-current indirect hot air spray dryer under following conditions.
Inlet temperature: 160° C.
Outlet temperature: 80° C.
Atomizer RPM: 12000
The yield is 9 gms. (The HPLC showed 35% Trigonelline & 20% 4-Hydroxyisoleucine)

Example 3

1000 grams of fenugreek seeds having a moisture content less than 5% were flaked in a roller flaker to a thickness of 2 mm The flaked material is stalked in a column having a bed height of 300 mm. 5 liters of hexane was passed through the layer of fenugreek and the eluent collected from the bottom is recycled through the fenugreek layer for a period of 10 hrs at 35° C. After 10 hrs the fenugreek layer was drained free of hexane. Solvent mixture (8 liters) comprising of Ethyl alcohol and water in the ratio of 3.5:1 was passed through the layer for a period of 8 hrs at 35° C. by recycling the eluent. After 8 hrs the fenugreek bed is drained free of extracts and all the collected extracts were concentrated to semisolid mass under vacuum at 50° C.

The concentrated mass is redissolved in 5 liters of deionised water to get a clear solution. The clear aqueous solution was passed through a column containing 400 ml of strong acid cation exchange Gel type resin for 2 hrs. TLC screening for the absence of Trigonelline checked on the column eluent using a system consisting of n-Butanol:Acetic acid:Water in the ratio of 12:8:4 as the mobile phase on silica Gel precoated plateF254 (1.05554.007) and observation under UV 254 nm. After saturation of the column the resin bed was washed free of colors and adhering impurities using 4 liters of deionised water. The column is desorbed using 800 ml of aqueous ammonia of 5N strength at a rate of 400 ml per hour. The mixture eluted out is concentrated under vacuum at 45° C. to a semisolid mass.

The dried mass is redissolved in 150 ml of deionised water and filtered free of insoluble. The solution is concentrated under vacuum at 50° C. to a solid content of 20% and spray dried in a co-current indirect hot air spray dryer under following conditions.
Inlet temperature: 160° C.
Outlet temperature: 80° C.
Atomizer RPM: 12000
The yield is 10 gms. (The HPLC showed 35% Trigonelline & 18% 4-Hydroxyisoleucine amino acid)

The above material is redissolved in 250 ml of Ethyl alcohol, filtered through 41Whatmann filter paper and cooled to 0° C. A dry stream of Hydrogen chloride gas is passed through this to precipitate the Trigonelline hydrochloride. The precipitate was filtered out on filter paper and washed with cold ethyl alcohol and dried under vacuum at 60° C.

Example 4

1000 grams of green *Coffea Arabica* seeds having moisture content less than 15% were flaked in a roller flaker to a thickness of 2 mm. The flaked material is stalked in a column having abed height of 500 mm. Solvent mixture (8 liters) comprising of water and Ethyl alcohol in the ratio of 9:1 was passed through the layer for a period of 8 hrs at 35° C. by recycling the eluent. After 8 hrs the *Coffea Arabica* bed is drained free of extracts and all the collected extracts were concentrated to semisolid mass under vacuum at 50° C.

The concentrated mass is redissolved in 5 liters of deionised water to get a clear solution. The clear aqueous solution was passed through a column containing 400 ml of strong acid cation exchange Gel type resin for 2 hrs. TLC screening for the absence of Trigonelline checked on the column eluent using a system consisting of n-Butanol:Acetic acid Water in the ratio of 12:8:4 as the mobile phase on silica Gel precoated plateF254 (1.05554.007) and observation under UV 254 nm. After saturation of the column the resin bed was washed free of colors and adhering impurities using 4 liters of deionised water. The column is desorbed using 800 ml of aqueous ammonia of 5N strength at a rate of 400 ml per hour. The mixture eluted out is concentrated under vacuum at 45° C. to a semisolid mass.

The dried mass is redissolved in 150 ml of deionised water and filtered free of insoluble. The solution is concentrated under vacuum at 50° C. to a solid content of 20% and spray dried in a co-current indirect hot air spray dryer under following conditions.
Inlet temperature: 160° C.
Outlet temperature: 80° C.
Atomizer RPM: 12000
The yield is 5 grams. (The HPLC showed 60% Trigonelline & remaining amino acids)

The above material is redissolved in 200 ml of Ethyl alcohol, filtered through 41whatmann filter paper and cooled to 0° C. a dry stream of Hydrogen chloride gas is passed through this to precipitate the Trigonelline hydrochloride. The precipitate was filtered out on filter paper and washed with cold ethyl alcohol and dried under vacuum at 60° C.

Example 5

1000 grams of green *Coffea Arabica* seeds free of parchment is pulverized in a Commuting mill to a 100% passing through a 20 mesh size. The broken seeds are boiled with 6 liters of deionised water at 95 to 100° C. for 4 hrs and filtered clear of all insoluble through filter cloth. The clear solution is cooled to room temperature and passed through an ion exchange resin column containing 500 ml of freshly regenerated strong acid cation exchange resin over a period of 3 hrs. The bottom eluent was monitored for the absence of Trigonelline using TLC system comprising of N-Butanol:acetic acid:water in the ratio of 10:8:5 and visualization through UV at 254 nm.

The column was washed free of all colors and impurities using 5 liters of Dematerialized water. The column is eluted with 600 ml of 6% ammonia solution and checked for the completion elution using the TLC system mentioned previously. The eluted liquid is concentrated at 50° C. under vacuum to a paste. The paste is triturated with 100 ml of 20% Hydrochloric acid gas in Isopropyl alcohol at 75° C. for 3 hrs and cooled to room temperature. The resultant precipitate is filtered and washed free of colours with 500 ml of isopropyl alcohol. The solid is dried at 80° C. under vacuum to get 10 grams of free flowing powder.

The following examples were conducted with the novel composition comprising trigonelline and 4 HI as well as trigonelline derivative (hydrochloride) and 4 HI derivative (hydrochloride).

Example 6

Haloperidol Induced Catalepsy in Mice

Haloperidol is neuroleptic agent that blocks the Dopamine D2 receptor in the brain. This precipitates the extra-pyramidal side effects which can be measured by the "Bar Test for catalepsy in mice". Catalepsy in mice is defined as a failure to correct an externally imposed unusual posture over a prolonged period of time. This catalepsy in mice is comparable to the akinesia, muscle rigidity and tremors seen in subjects with Parkinson's disease. Haloperidol induced catalepsy can be reversed if dopaminergic drugs that supply dopamine to the striatum of the brain since it increase competitive antagonism.

Procedure: Swiss Albino mice of either sex weighing 23-28 g are used. Catalepsy was induced by Haloparidol (0.5 mg/kg i.p.) and assessed by bar test up to 3 hrs. Six animals are dosed with the saline, test drug and the standard intraperitonially. The animals are placed in translucent plastic boxes with a wooden dowel mounted horizontally 2.5 cm from the floor of the box. The animals are allowed to adapt to the box for 2 min. Then, each animal is grasped gently around the shoulders and under the forepaws and placed carefully on the dowel. The amount of the time spent with at least one forepaw on the bar is determined. When the animal removes its paws, the time is recorded and the mice are repositioned on the bar. Three trials are conducted for each animal at 30, 60, 120 and 360 min, with 6 animals in each group.

Figure 1:
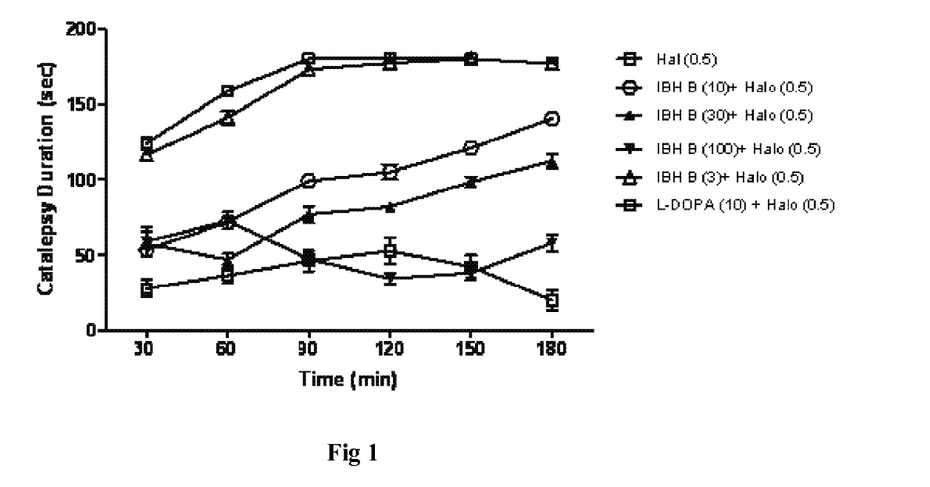
FIG. 1: shows dose dependent response of the test drug in the reduction of catalepsy. The plot indicates IBH-B as the test drug of the invention. All values for IBH-B (10, 30 or 100)+Hal (0.5) and L-DOPA (10)+Hal (0.5) are significant at $P<0.001$ and IBH-B (3)+Hal (0.5) is non-significant as compared with Hal (0.5) at respective time. Treatment of IBH-B significantly reduced Haloperidol induced catalepsy.

The test drug has shown significant dose dependant response in reducing catalepsy (FIG. 1). The effects of the standard drug L-Dopa at a dosage of 10 mg/kg was found to be more effective than the test drug at a dosage of 100 mg/kg. Although this difference is significant, the test drug proved to be fast acting and devoid of the "ON-OFF" action present in standard drugs. Also the standard drug showed a decline in the reduction of catalepsy after the initial effect on the catalepsy. This confirms Dopaminergic action of the test drug (FIG. 1). Thus it can be seen that the test drug is reversing the induced symptoms of Parkinson by Haloparidol.

The reversal of haloperidol induced catalepsy confirms the ability of the test drug composition to minimize the side effects caused by haloperidol which is a dopamine receptor antagonist. Hence this shows that the drug is a dopaminergic agent which can be used to minimize the effects of dopamine receptor antagonists including anti-psychotic drugs.

Example 7

Oxotremorine Antagonism

Oxotremorine is a cholinergic drug which is a muscarine agonist and induces parkinsonism-like signs such as tremors, ataxia, spasticity, salivation, lacrimation and hypothermia. Oxotremorine is a cholinergic drug, which induces excessive tremors in mice. If a drug is having anti-cholinergic property like atropine the tremors will be decreased.

Procedure: Groups of 6-10 male NMRI mice weighing 18-22 g are used. They are dosed orally with the test compound or the standard (5 mg/kg benezatropine mesilate) 1 hour prior to the administration of 0.5 mg/kg oxotremorine. Tremor is scored after oxotremorine dosage in periods of 5 min for 1 hour.

After the administration of 0.5 mg/kg of Oxotremorine, the tremors started within 15 mins and were sustained for 30 mins.

Parameters:

| Tremor Score | | Salivation and Lacrimation 30 mins after oxotrmorine injection | |
|---|---|---|---|
| Absent | 0 | Absent | 0 |
| Slight | 1 | Slight | 1 |
| Medium | 2 | Medium | 2 |
| Severe | 3 | Severe | 3 |

No. of animals used in each group n=6
Tremor Score

| Category | Tremor score 5 minutes | Tremor score 15 minutes | Tremor score 30 minutes | Tremor score 45 minutes |
|---|---|---|---|---|
| Control group only oxytremorine n = 6 | 3.0 | 2.8 | 2.7 | 2.6 |
| Test compound group 30 mg/kg and oxytremorine n = 6 | 2.7 | 2.6 | 2.5 | 2.5 |
| Test compound group 100 mg/kg and oxytremorine n = 6 | 1.6 | 1.6 | 1.8 | 1.9 |
| Test compound group 200 mg/kg and oxytremorine n = 6 | 1.6 | 1.6 | 1.7 | 1.6 |
| Positive control atropine 5 mg/kg and oxytremorine n = 6 | 0.9 | 0.9 | 1.0 | 1.3 |

Test compound has shown significant activity by decreasing the tremor score at 100 mg/kg and 200 mg/kg dose. This activity is consistent and is sustained up to 45 minutes. The activity at 30 mg/kg is low. Positive control atropine has the test activity but decreases with time. Thus the test drug is reversing Parkinson's symptoms by mild Anticholinergic Activity.

Salivation and Lacrimation Score

| Category | Salivation score at 30 minutes | Lacrimation score at 30 minutes |
|---|---|---|
| Control group only oxytremorine n = 6 | 3.0 | 2.9 |
| Test compound at 30 mg/kg | 2.5 | 2.6 |
| Test compound at 100 mg/kg | 1.6 | 1.7 |
| Atropine | 0.8 | 0.6 |

Test compound has shown reduction in salivation score. However, it is not as powerful as atropine thereby indicating mild Anticholinergic effect. The lacrimation also gets reduced. However, it is not as powerful as Atropine.

Figure 2:
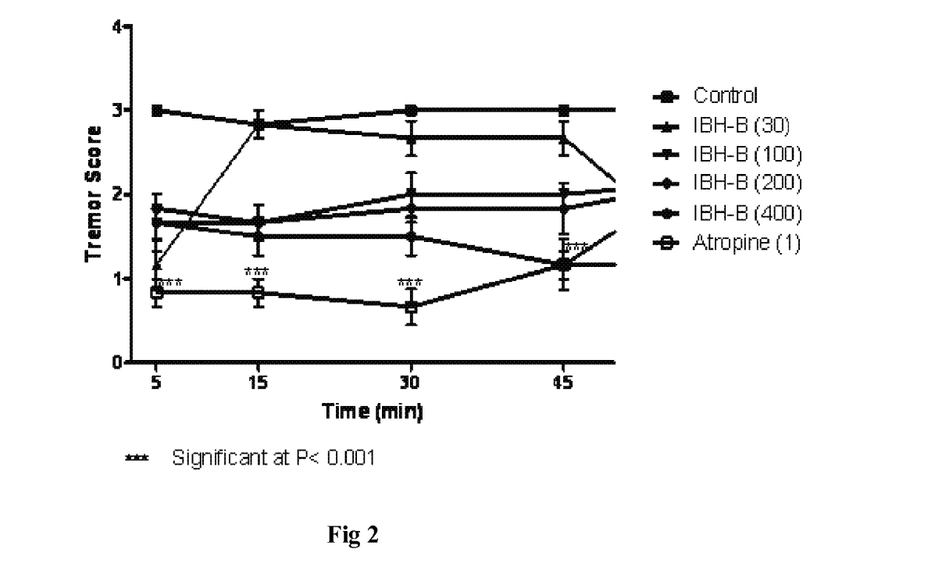
FIG. 2: shows significant decrease in the tremor score by the test drug indicated as IBH-B in the plot.

Atropine 1 mg/kg and the test drug at 100, 200 and 400 mg/Kg cause significant decrease in severity of tremors (FIG. 2) and is insignificant at dose 30 mg/kg. The drug is showing maximum effect at 30 min and it is started reversing after 45 min. Hence the test drug has anti-cholinergic property at very high doses.

Example 8

6-Hydroxydopamine Model

6-Hydroxydopamine (6-OHDA) is a neurotoxin which causes a unilateral lesion of the dopaminergic nigrostriatal pathway that induces hypersensitivity of the post synaptic dopaminergic receptor in the striatum of the lesioned side. An indirect acting compound like amphetamine is administered the mice rotate toward the lesioned side (ipsilateral) as opposed to when a direct acting dopaminergic drug is administered which causes then to rotate contra laterally. Therefore, this test can be used for the study of central dopamine function and the evaluation of dopamine antagonists and agonists, particularly the activity of novel anti-parkinsonian drugs. This test clearly distinguishes drugs with predominantly dopamine receptor agonist activity from those with predominantly dopamine releasing activity of the drug.

Procedure: Male Wistar mice weighing 200-250 grams at the time of surgery are used. They are housed individually in a controlled environment with free access to food and water. The animals are anaesthetized with sodium pentobarbital. The head is placed in a stereotaxic device (DKI 900) and positioned according to the atlas of Konig and Klippel. After a sagittal cut is made in the skin of the skull, a 2 mm wide hole is drilled with an electrical trepan drill. Care is taken not to lesion the meninges. A 30 gauge stainless-steel cannula connected to a Hamilton syringe is aimed at the anterior zona compacta of the substantia nigra (coordinates anterior 1.88 mm, lateral 2.0 mm and dorso-ventral—8.2 mm from instrument zero). A total of 8 µg of 6-HAD in 4 γ/L of saline is injected at a rate of 1 γ/L/min. After the intra-cranial injection, the wound is closed.

The animal is allowed several weeks for recovery and for development of the lesion. Specially constructed opaque plastic spheres attached to solid state programming equipment serve as test chambers. The number of full turns, either ipsilateral or contra lateral to the lesion, are recorded on an automatic printout counter every 15 min for one or two hours test sessions. To determine the control values for ipsilateral turning, each subject is administered 2.5 mg/kg of d amphetamine and immediately placed in the circling chamber for 2 hours Control values for contra lateral circling are determined by injecting apomorphine at 1 mg/kg s.c. and recording the rat's circling for 1 hour. Test compounds are given i.p or sc. And the animals placed into the circling chambers. Circling is recorded over a 1 hour period. This experiment is conducted in 30 animals and the average is represented in the table

| Drug & Dosage | Contra-lateral Rotation | Ipsilateral Rotation |
|---|---|---|
| Sterile Water | 1 | 0.33 |
| Test Drug (10 mg/kg) | 0.67 | 5.33 |
| Test Drug (30 mg/kg) | 0.83 | 30.67 |
| Test Drug (100 mg/kg) | 0.35 | 10.4 |
| Apomorphine (0.3 mg/kg) | 169.33 | 0.67 |
| L-Dopa (10 mg/kg) | 45.67 | 0.83 |

The test drug induced significant ipsilateral rotations at dose 30 mg/kg ($P<0.001$) and 10 mg/kg ($P<0.05$). This test mimics dopamine depletion and consequently Parkinson's disease. Anti-Parkinson's compounds may have contra-lateral or ipsilateral rotation. Drugs like Amphetamine induce ipsilateral rotation. Whereas drugs like L-Dopa, Apomorphine, Bromocriptine induce contralateral rotation. Monoamine Oxidase B inhibitors like Selgiline induces ipsilateral rotation. COMT inhibitors induce contra-lateral rotation.

The test drug behaves like Amphetamine or Monoamine Oxidase (MAO-B) inhibitor. Hence the test drug may have the dopamine releasing property that is significant as compared to control at these doses.

This model is an important one to determine whether a compound is a dopaminergic one or one that acts on the dopamine receptors. The ipsilateral rotation with the test compound shows its dopaminergic activity. Unlike the current class of drugs which show a contralateral rotation the test compound is a dopaminergic agent and not a receptor agonist.

This experiment proves the exclusive dopaminergic activity of the test drug. Hence this dopaminergic composition can find applications related to increase of levels of dopamine. Increased levels of dopamine have an inhibitory effect on prolactin levels. Increased prolactin levels are one of the causes of PCOS and infertility. This dopaminergic compound inhibits prolactin levels by increasing dopamine levels.

This dopaminergic compound also finds applications as a muscle relaxant.

Example 9

Testing the Effects of the Test Drug on MPTP Treated Mice

This test determines the extent of effect on the locomotor activity of MPTP (Methyl Phenyl TetraPyridine) treated mice when they are pre-treated and post-treated with the test drug.

When MPTP is administered through the systemic route it causes transient impairment of the dopamine system function. This test helps to determine the pathophysiology of neurodegenerative processes as well as the effects of neurotrophic and neuro-protective agents.

MPTP significantly decreases the locomotor activity of the mice. The test drug's efficiency is measured based on the percentage increase in the motor activity in the MPTP treated mice.

The locomotor activity is measured in terms of:
1. Spontaneous motor activity

| Treatment | Mean ± SEM | % Increase |
|---|---|---|
| Untreated | 868.166 ± 17.377 | — |
| MPTP | 290.166 ± 18.679$^{\#\#\#\#}$ | — |
| Test Drug (Pre): Prophylactic | 564.166 ± 24.106*** | 94.43% |
| Test Drug (Post): Therapeutic | 280.500 ± 23.891$^{ns}$ | −3.33% |

Pre-treatment of the mice with the test drug significantly reduced the effect of MPTP. Although the pre-treatment gave good results, the treatment of the mice with the test drug, post the treatment with MPTP did not show an increase in the motor activity.

2. Number of squares crossed in an open field

| Treatment | Mean ± SEM | % Increase |
|---|---|---|
| Untreated | 465.500 ± 18.005 | — |
| MPTP | 122.333 ± 8.151$^{\#\#\#\#}$ | — |
| Test Drug (Pre): Prophylactic | 250.166 ± 12.908*** | 104.49% |
| Test Drug (Post): Therapeutic | 143.166 ± 12.475$^{ns}$ | 17.03% |

The pre-treatment with the test drug drastically increased the number of squares crossed by the mice, while post-treatment with the test drug did not show a very significant increase.

3. Total distance travelled in an open field

| Treatment | Mean ± SEM | % Increase |
|---|---|---|
| Untreated | 698.250 ± 27.008 | — |
| MPTP | 183.500 ± 12.227$^{\#\#\#\#}$ | — |
| Test Drug (Pre): Prophylactic | 375.250 ± 19.363*** | 104.49% |
| Test Drug (Post): Therapeutic | 214.750 ± 18.713$^{ns}$ | 17.03% |

The pre-treatment with the test drug drastically increased the distance travelled by the mice, while post-treatment with the test drug did not show a very significant increase.

4. Total movement time in an open field

| Treatment | Mean ± SEM | % Increase |
|---|---|---|
| Untreated | 233.420 ± 7.322 | — |
| MPTP | 217.330 ± 8.979 | — |
| Test Drug (Pre): Prophylactic | 235.350 ± 9.001 | 8.29% |
| Test Drug (Post): Therapeutic | 242.790 ± 13.503 | 11.71% |

No significant time change was observed during the pre/post-treatment with the test drug on the MPTP treated mice.

5. Average Speed in an open field

| Treatment | Mean ± SEM | % Increase |
|---|---|---|
| Untreated | 2.999 ± 0.124 | — |
| MPTP | 0.846 ± 0.051 | — |
| Test Drug (Pre): Prophylactic | 1.595 ± 0.059*** | 88.53% |
| Test Drug (Post): Therapeutic | 0.890 ± 0.079$^{ns}$ | 5.2% |

Pre-treatment of the mice with the test drug significantly increased the average speed of the mice, while post-treatment showed no increase in the speed.

Thus by the above experiments it is observed that the composition prepared by the above mentioned process has potent dopaminergic activity, and is an MAO inhibitor. This optimum dosage of the drug does not show anti-cholinergic activity, which is seen at very high doses of the drug.

Example 10

Effect of Test Drug on Tyramine Potentiation

Non-selective MAO inhibitors when used as neuropsychiatric drugs cause a condition called tyramine potentiation. Tyramine is an amino acid which is a precursor for the mono amine noradrenaline. Monoamine oxidase-A (MAO-A) is an enzyme which prevents the conversion of tyramine to noradrenaline. Thus in the presence of drugs which act like MAO-A inhibitors the levels of noradrenaline is high. Most fermented foods, like cheese, wine etc, have a high percentage of tyramine. Thus when foods like these are ingested by a subject who is consuming MAO-A inhibitors, there is a sudden surge in the tyramine level and subsequently the level of noradrenaline also rises. This sudden increase in the level of noradrenaline drastically increases the blood pressure and can lead to fatal consequences.

The tyramine potentiation test is conducted to determine the selectivity of the test drug for MAO-A/B. For an accurate determination of this test, the study was carried out in an acute and chronic environment of the drug.

Figure 3:
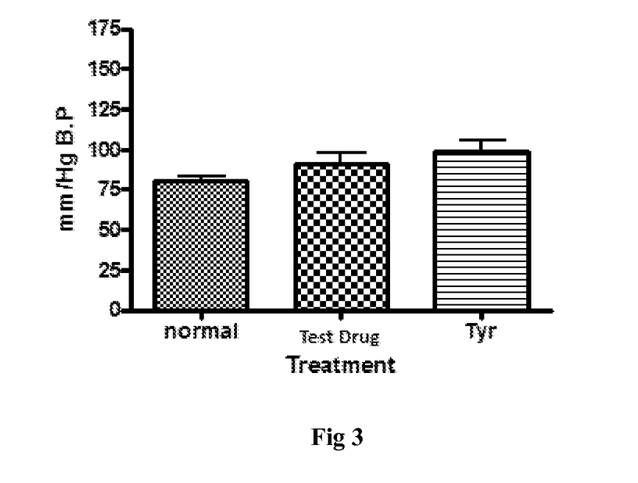
FIG. 3: shows the effect of test drug on tyramine potentiation (acute study).
Figure 4:
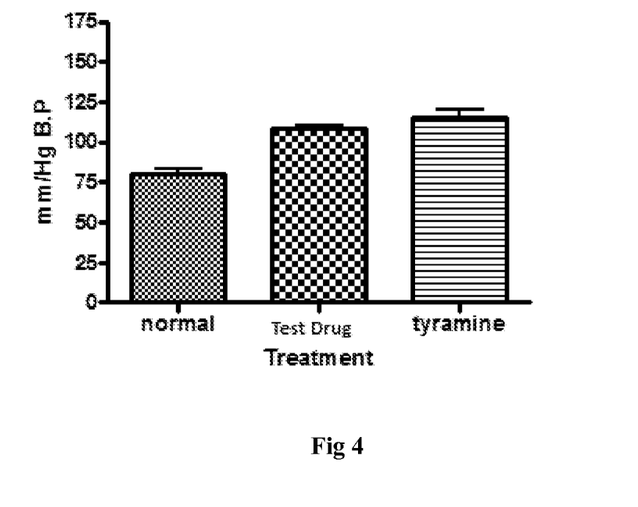
FIG. 4: shows the effect of test drug on tyramine potentiation (chronic study).

Acute Study: In the acute study the male Wistar rats (n=5) were taken were anesthetized by injecting urethane solution (1.25 g/kg, i.p.). Body temperature was maintained at 37° C. and the trachea was cannulated to maintain airways. (Blood pressure) instruments inserted in the canulas to the left carotid artery and the jugular vein for blood pressure (BP) monitoring and drug administration, respectively. The arterial catheter was connected to the pressure transducer to measure the blood pressure using four channel physiological recorder systems. The effects of the test drug (30 mg/kg p.o.) to the Tyramine (5 mg/kg i.v.) were recorded (FIG. 3).
The study conducted has 3 groups:
Group 1: Normal
Group 2: Tyramine+Test Drug
Group 3: Tyramine alone Chronic Study: The male Wistar rats (n=5) were administered with test drug (30 mg/kg p.o.) for one month. Body temperature was maintained at 37° C. and the trachea was cannulated to maintain airways. Instruments inserted in the canulas to the left carotid artery and the jugular vein for blood pressure (BP) monitoring and drug administration, respectively. The arterial catheter was connected to the pressure transducer to measure the blood pressure using four channel physiological recorder systems. The effects of the test drug (30 mg/kg p.o.) to the Tyramine (5 mg/kg i.v.) were recorded (FIG. 4).
The study conducted has 3 groups:
Group 1: Normal
Group 2: Tyramine+Test Drug
Group 3: Tyramine alone In both the acute and the chronic study, the test drug did not show any raise in blood pressure thus establishing that these are not MAO-A inhibitors. Tyramine causes a slight increase in blood pressure, the current class of MAOIs usually cause a drastic increase in blood pressure (tyramine potentiation). Hence from the graphs seen in the Acute and Chronic Study, the test drug does not potentiate an increase in blood pressure.

Hence the test drug is deemed to be a MAO-B inhibitor, which does not cause tyramine potentiation and has no interaction with tyramine ingested from foods in the diet. This is a major advantage of the test drug over the existing class of drugs.

Example 11

Evaluate an in Enzyme Assay of the Test Drug

Figure 5:
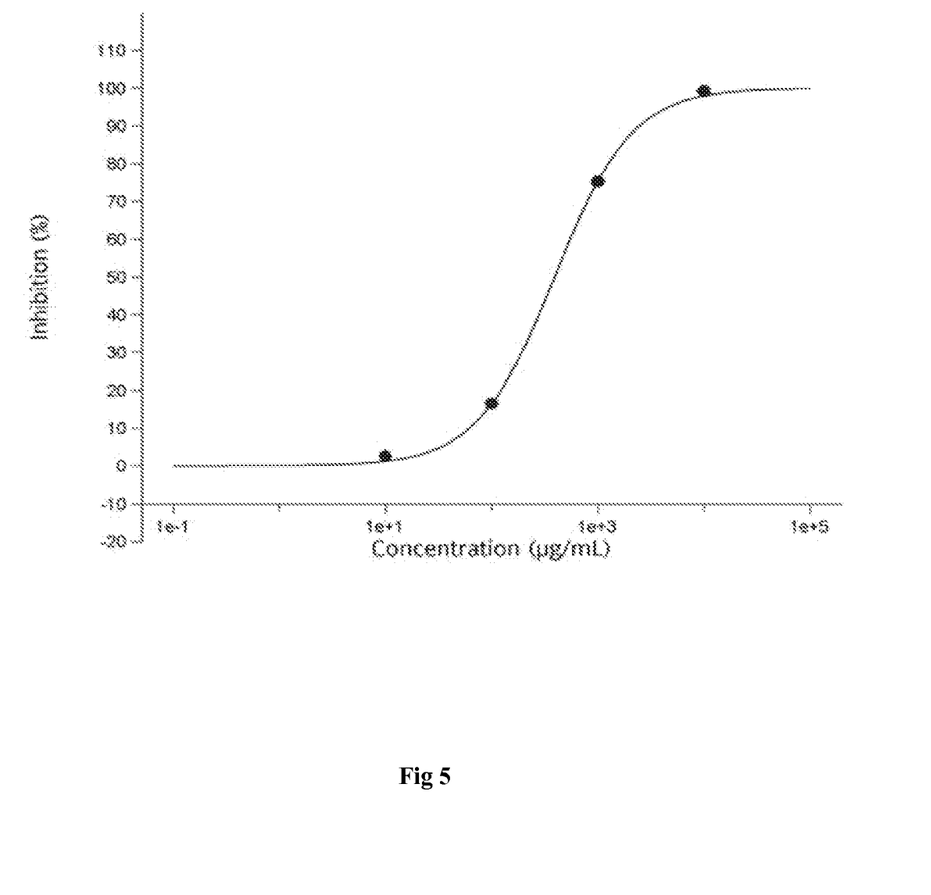
FIG. 5: The response curve illustrating the selective inhibition of MAO-B by the test compound.

The inhibition curves for this experiment are shown in FIG. 5. These enzyme assays were carried out as per the references
Youdim M B and Finberg J P (1991)
New directions in monoamine oxidase A and B selective inhibitors and substrates. Biochem Pharmacol. 41(2): 155-162
Urban P, Andersen J K, Hsu H P and Pompon D (1991)
Comparative membrane locations and activities of human monoamine oxidases expressed in yeast. FEBS Lett. 286 (1-2): 142-146.

This experiment measures the ability of the test drug composition F-1 in the inhibition of the enzyme monoamine oxidase. MAOs are an enzymes that catalyze the oxidation of monoamines. In humans there are two types of MAOs—MAO A and MAO B. Both these enzymes are found in the neurons and astroglia as well as outside the CNS.
Outside the CNS MAOs are found:
MAO-A: Liver, gastrointestinal tract and placenta
MAO-B: Platelets Both MAOs are also vital to the inactivation of monoaminergic neurotransmitters, for which they display different specificities.
MAO-A: Breakdown of Serotonin, norepinephrine (noradrenaline), and epinephrine (adrenaline).
MAO-B: Breakdown of Phenethylamine.
Both forms of MAOs break down dopamine.

The present classes of MAO inhibitors usually have an interaction with foods that have high tyramine levels like cheeses, pickled foods, chocolates, beer, wine and certain meats. The interaction of tyramine with MAOIs can cause a dangerously high increase in blood pressure, which can lead to a stroke.

The response curves that illustrate the selective inhibition of MAO-B by the test compound is shown in FIG. 5. This graph illustrates the inhibition of MAO-B by the test drug which is very useful in the treatment of dopamine related diseases including Parkinson's disease.

The tyramine potentiation experiment conducted in Example 10 shows that the test drug does not have an increasing effect on blood pressure and hence is safe for use in a subject in need thereof.

Example 12

For Human doses
1) For therapeutic application of management of Parkinsons disease a human dose of 0.5 mg per kg to 20 mg per kg daily as a single dose or triturated into three equal doses per day.
2) For therapeutic dose in decreasing the level of prolactin which is implicated in loss of libido and sexual dysfunction, a daily recommended dose of 0.5 mg per kg of body weight to 25 mg per kg of body weight as a single dose or triturated into 3 equally divided doses.
3) Therapeutic dose for stopping lactation in nursing mothers 0.5 mg per kg to 20 mg per kg of body weight daily.
4) For muscle relaxation in exercise physiology the recommended dose is 0.25 mg per kg to 17 mg per kg of body weight.
5) For mental alertness and performance enhancement the recommended daily dose is 0.25 mg per kg to 15 mg per kg of body weight.

The invention claimed is:
1. A process of preparing a pharmaceutical composition having dopaminergic related pharmaceutical activities comprising trigonelline hydrochloride and 4-hydroxyisoleucine hydrochloride, optionally along with excipients(s), wherein the concentration of trigonelline hydrochloride ranges between 31% to 90%, said process comprising steps of:
a. extracting a clear solution containing trigonelline and 4-hydroxyisoleucine from plant source; and b. optionally precipitating hydrochloride derivative of trigonelline and 4-hydroxyisoleucine from the clear solution and obtaining said composition.

2. The process as claimed in claim 1, wherein the concentration of 4-hydroxyisoleucine hydrochloride ranges between 10% to 30%; and the trigonelline hydrochloride is derived from trigonelline and the 4-hydroxyisoleucine hydrochloride is derived from 4-hydroxyisoleucine.

3. The process as claimed in claim 1, wherein the excipient (s) are selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents and spheronization agents.

4. The process as claimed in claim 1, wherein the clear solution is extracted from plant *Trigonella foenum graecum* and/or *Coffea arabica* comprising steps of:
   a. flaking seeds of *Trigonella* and/or *Coffea arabica*;
   b. defatting flaked *Trigonella* seeds using hexane solvent;
   c. passing a solvent mixture of aliphatic alcohol and water through the flaked seeds to extract a solvent containing trigonelline and amino acid(s);
   d. vacuum concentrating the solvent to obtain semisolid mass;
   e. dissolving the semisolid mass in deionized water to obtain a clear solution;
   f. passing the clear solution of step (e) through an ion exchange resin column to retain the amino acids and the trigonelline;
   g. eluting the column and concentrating the eluent to obtain resultant mass;
   h. drying the clear solution of the resultant mass to obtain a free flowing powder; and
   i. dissolving the powder in a solvent to obtain said clear solution containing trigonelline and amino acid(s).

5. The process as claimed in claim 4, wherein the seeds are flaked to a size preferably of about 2 mm thickness; the solvent mixture comprises an aliphatic alcohol and water in ratio of 1:9 to 9:1, preferably 7:3; and the aliphatic alcohol is ethanol.

6. The process as claimed in claim 4, wherein the column is eluted with aqueous or alcoholic solution of ammonia; the solvent is selected from a group comprising, aliphatic alcohols, ketones, and mixtures of one or more thereof; and the solvent is ethanol.

7. The process as claimed in claim 4, wherein the concentration is carried at a temperature ranging from 40° C. to 80° C. and the amino acid is 4-hydroxyisoleucine.

8. A method of treating dopamine related diseases, said method comprising administering a therapeutically effective amount of a pharmaceutical composition having dopaminergic related pharmaceutical activities comprising trigonelline hydrochloride and 4-hydroxyisoleucine hydrochloride, optionally along with excipients(s) in a subject in need thereof, wherein the concentration of trigonelline hydrochloride ranges between 31% to 90%.

9. The method as claimed in claim 8, wherein the subject is animal including human beings and the concentration of 4-hydroxyisoleucine hydrochloride ranges between 10% to 30%.

10. A method of treating ill effects caused by prolactin, said method involves prolactin inhibition by administering a therapeutically effective amount of a pharmaceutical composition having dopaminergic related pharmaceutical activities comprising trigonelline hydrochloride and 4-hydroxyisoleucine hydrochloride, optionally along with excipients(s) in a subject in need thereof, wherein the concentration of trigonelline hydrochloride ranges between 31% to 90%.

11. The method as claimed in claim 10, wherein the ill effects caused by prolactin are selected from the group consisting of infertility, polycystic ovary disease, and increased lactation.

12. The method as claimed in claim 10, wherein the subject is animal including human beings and the concentration of 4-hydroxyisoleucine hydrochloride ranges between 10% to 30%.

13. A method of treating side-effects caused by dopamine receptor antagonists, said method comprising administering a therapeutically effective amount of a pharmaceutical composition having dopaminergic related pharmaceutical activities comprising trigonelline hydrochloride and 4-hydroxyisoleucine hydrochloride, optionally along with excipients(s) in a subject in need thereof, wherein the concentration of trigonelline hydrochloride ranges between 31% to 90%.

14. The method as claimed in claim 13, wherein the side-effects are the movement disorders caused by blockage of dopamine receptor by dopamine receptor antagonists.

15. The method as claimed in claim 13, wherein the subject is animal including human beings and the concentration of 4-hydroxyisoleucine hydrochloride ranges between 10% to 30%.

* * * * *